(12) United States Patent
Smith (10) Patent No.: US 11,350,838 B2
(45) Date of Patent: Jun. 7, 2022

(54) PRESSURE CATHETER DEVICE

(71) Applicant: Laborie Medical Technologies, Corp., Mississauga (CA)

(72) Inventor: Bryce Smith, Sandy, UT (US)

(73) Assignee: Laborie Medical Technologies Corp., Portsmouth, NH (US)

(*) Notice: Subject to any disclaimer, the term of this patent is extended or adjusted under 35 U.S.C. 154(b) by 760 days.

(21) Appl. No.: 15/456,002

(22) Filed: Mar. 10, 2017

(65) Prior Publication Data
US 2017/0258345 A1 Sep. 14, 2017

Related U.S. Application Data

(60) Provisional application No. 62/306,828, filed on Mar. 11, 2016.

(51) Int. Cl.
*A61B 5/03* (2006.01)
*A61M 25/10* (2013.01)
(Continued)

(52) U.S. Cl.
CPC .............. *A61B 5/036* (2013.01); *A61B 5/205* (2013.01); *A61B 5/6853* (2013.01);
(Continued)

(58) Field of Classification Search
CPC ........... A61B 5/036; A61B 5/03; A61B 5/033; A61B 5/035; A61B 5/205; A61B 5/204;
(Continued)

(56) References Cited

U.S. PATENT DOCUMENTS 5,135,484 A * 8/1992 Wright .................. A61B 17/22
604/101.03
5,573,007 A 11/1996 Bobo, Sr.
(Continued)

FOREIGN PATENT DOCUMENTS

CN 1859942 A 11/2006
CN 104470576 A 3/2015
(Continued)

OTHER PUBLICATIONS

Yamashita, Noboru et al. "Preparation and characterization of gelatin sponge millispheres injectable through microcatheters", Medical Devices: Evidence and Research, 2009:2 19-25 (Year: 2009).*

(Continued)

*Primary Examiner* — Matthew Kremer
*Assistant Examiner* — Avery M Foley
(74) *Attorney, Agent, or Firm* — Fredrikson & Byron, P.A.

(57) ABSTRACT

This disclosure provides apparatus and methods for detecting pressure changes within a cavity of a patient. A pressure-sensing catheter comprises an elongate member and a monitor lumen. The pressure-sensing catheter may have a hollow pressure-compliant member in fluid communication with the monitor lumen and thereby define a fluid column. A connector apparatus can be in fluid communication with the monitor lumen, and can comprise a first complementary connector and a second complementary connector. One of the first complementary connector and the second complementary connector can have a pressurizing device that can displace a volume of fluid located within a bore of the other complementary connector into the fluid column, wherein the ratio of the volume of displaced fluid to the volume of the fluid column ranges from about 1:2 to about 1:4. The (Continued)

pressure catheter can comprise a radio-opaque band circumscribing the exterior of the elongate member.

13 Claims, 11 Drawing Sheets (51) Int. Cl.
*A61B 5/20* (2006.01)
*A61B 5/00* (2006.01)
*A61M 25/00* (2006.01)

(52) U.S. Cl.
CPC ........ *A61M 25/0026* (2013.01); *A61M 25/10* (2013.01); *A61B 2562/0247* (2013.01); *A61M 25/1011* (2013.01); *A61M 2025/0001* (2013.01); *A61M 2025/0003* (2013.01); *A61M 2025/1079* (2013.01); *A61M 2205/32* (2013.01)

(58) Field of Classification Search
CPC .................. A61B 5/207; A61B 5/6853; A61B 2562/0247; A61M 25/0026; A61M 25/0028; A61M 25/10; A61M 25/1002; A61M 25/1018; A61M 25/10187; A61M 25/1025; A61M 25/1011; A61M 2025/1013; A61M 2025/1015; A61M 2025/0001; A61M 2025/0002; A61M 2025/0003; A61M 2025/1079; A61M 2025/32; A61M 25/10184
See application file for complete search history.

(56) References Cited

U.S. PATENT DOCUMENTS

| | | |
|---|---|---|
| 5,647,847 A | 7/1997 | LaFontaine et al. |
| 5,776,116 A | 7/1998 | Lopez et al. |
| 5,795,325 A * | 8/1998 | Valley .............. A61B 17/12022 604/103.1 |
| 6,421,013 B1 | 7/2002 | Chung et al. |
| 6,649,829 B2 | 11/2003 | Garber et al. |
| 6,673,022 B1 * | 1/2004 | Bobo .................. A61B 5/031 600/561 |
| 6,837,864 B1 * | 1/2005 | Bertolero ............ A61M 25/003 604/4.01 |
| 7,352,771 B2 | 4/2008 | Garber |
| 7,926,856 B2 | 4/2011 | Smutney et al. |
| RE44,310 E | 6/2013 | Chadbourne et al. |
| 2004/0127813 A1 | 7/2004 | Schwamm |
| 2005/0064223 A1 * | 3/2005 | Bavaro ................ A61B 5/1076 428/615 |
| 2005/0187430 A1 | 8/2005 | Aundal et al. |
| 2005/0215119 A1 | 9/2005 | Kaneko |
| 2006/0148279 A1 | 7/2006 | German et al. |
| 2007/0252771 A1 | 11/2007 | Maezawa et al. |
| 2007/0273525 A1 | 11/2007 | Garber et al. |
| 2008/0030343 A1 | 2/2008 | Raybuck et al. |
| 2009/0009290 A1 | 1/2009 | Kneip et al. |
| 2009/0171278 A1 * | 7/2009 | Hirszowicz ...... A61B 17/22012 604/97.01 |
| 2009/0306539 A1 * | 12/2009 | Woodruff ............... A61B 5/205 600/561 |
| 2010/0001516 A1 | 1/2010 | Pisula, Jr. et al. |
| 2010/0249663 A1 * | 9/2010 | Nishtala ................ A61B 5/036 600/587 |
| 2010/0249723 A1 | 9/2010 | Fangrow, Jr. |
| 2010/0280451 A1 * | 11/2010 | Teeslink ........... A61B 17/12045 604/99.04 |
| 2011/0136550 A1 | 6/2011 | Maugars |
| 2011/0210541 A1 | 9/2011 | Lewis et al. |
| 2013/0015654 A1 | 1/2013 | Gilham et al. |
| 2013/0184612 A1 | 7/2013 | Quackenbush et al. |
| 2013/0197564 A1 * | 8/2013 | Levine .............. A61M 25/0141 606/200 |
| 2013/0268029 A1 | 10/2013 | Cauller et al. |
| 2013/0270820 A1 | 10/2013 | Py |
| 2014/0203077 A1 | 7/2014 | Gadh et al. |
| 2014/0266775 A1 * | 9/2014 | Moon .................... A61B 5/035 340/870.01 |
| 2015/0130408 A1 | 5/2015 | Wei |
| 2015/0135502 A1 | 5/2015 | Rankin et al. |
| 2015/0250974 A1 | 9/2015 | Bobo, Sr. et al. |
| 2016/0029912 A1 | 2/2016 | Stimpson |
| 2016/0046130 A1 | 2/2016 | Burdge et al. |
| 2016/0089254 A1 * | 3/2016 | Hopkinson ............. A61L 31/10 623/1.11 |
| 2016/0213228 A1 * | 7/2016 | Rohl .................... A61B 17/122 |
| 2017/0021144 A1 | 1/2017 | Kanner et al. |
| 2017/0140330 A1 | 5/2017 | Rinzler et al. |
| 2017/0259035 A1 | 9/2017 | Smith et al. |

FOREIGN PATENT DOCUMENTS

| | | |
|---|---|---|
| EP | 0774919 B1 | 11/2002 |
| EP | 1996851 B1 | 11/2011 |
| EP | 1799610 B1 | 11/2012 |
| EP | 1866611 B1 | 9/2014 |
| JP | 1996173542 A | 5/1996 |
| JP | 2003000718 A | 1/2003 |
| JP | 2006142032 A | 6/2006 |
| JP | 2007504850 A | 3/2007 |
| JP | 2009511149 A | 3/2009 |
| JP | 2009529937 A | 8/2009 |
| WO | 2005032639 A1 | 4/2005 |
| WO | 2005107006 A1 | 11/2005 |
| WO | 2009055435 A1 | 4/2009 |
| WO | 2014160300 A1 | 10/2014 |

OTHER PUBLICATIONS

International Patent Application No. PCT/US2017/021924, International Search Report and Written Opinion dated Jul. 28, 2017, 24 pages.
International Patent Application No. PCT/US2017/021924, Invitation to Pay Additional Fees and Partial Search Report dated Jun. 6, 2017, 19 pages.
Bryce Smith, U.S. Appl. No. 15/456,062, filed Mar. 10, 2017, entitled "Pressure Catheter and Connector Device," 48 pages.
English Abstract for Chinese Publication No. CN 1859942 A, published Nov. 8, 2006, 1 pgs.

* cited by examiner

PRESSURE CATHETER DEVICE

RELATED APPLICATIONS

This application claims the benefit of U.S. Provisional Patent Application No. 62/306,828 filed Mar. 11, 2016, the entire contents of which are incorporated herein by reference.

BACKGROUND

Pressure catheter devices typically include an elongate catheter having at least one gas-filled pressure monitoring lumen extending longitudinally through the catheter. A gas-filled membrane (e.g., a balloon) can be formed on the outer surface of the catheter. The gas-filled membrane can be in fluid communication with the gas-filled pressure monitoring lumen. Changes in pressure against the gas-filled membrane may result in changes in pressure of the gas within the gas-filled pressure monitoring lumen. A pressure transducer connected to the proximal end of the gas-filled pressure monitoring lumen can sense and display or record the changes in pressure which can be communicated through the gas-filled pressure monitoring lumen of the catheter.

Conventional pressure catheters may require a supplemental source of gas to refill the balloon due to gas diffusion out of the balloon during the procedure. The use of supplemental gas allows the balloon to continue to sense pressure changes within the body of the patient. In addition, dead space within the lumen reduces the ability of the pressure sensor to take accurate measurements over small discrete intervals.

SUMMARY

In one aspect, this disclosure provides a pressure-sensing catheter for detecting pressure changes within a cavity of a patient. The pressure-sensing catheter comprises an elongate member comprising a proximal end, a distal end and a central lumen extending from the proximal end to the distal end. Further, the pressure-sensing catheter comprises a monitor lumen positioned within the elongate member and extending from the proximal end to the distal end. The pressure-sensing catheter may have a hollow pressure-compliant member defining an interior chamber in fluid communication with the monitor lumen. The pressure-compliant member can be disposed about an exterior of the elongate member, wherein the monitor lumen and the interior chamber of the pressure-compliant member define a fluid column. A connector apparatus can be disposed about the proximal end and be in fluid communication with the monitor lumen, and can comprise a first complementary connector and a second complementary connector, at least one of which can be fluidly coupled to the fluid column, defined by the pressure-compliant member. Further, one of the first complementary connector and the second complementary connector can have a pressurizing device and the other of the first complementary connector and the second complementary connector can have a bore. The pressurizing device can displace a volume of fluid located within the bore into the fluid column, wherein the ratio of the volume of displaced fluid to the volume of the fluid column ranges from about 1:2 to less than about 1:1 (e.g., about 3:4).

In another aspect, the pressure catheter can comprise a radio-opaque band circumscribing the exterior of the elongate member and being disposed within the interior chamber of the pressure-compliant member.

In a further aspect, a method of detecting pressure changes within a cavity of a patient, comprises the step of advancing a catheter such as those disclosed according to any embodiment herein within the cavity of a patient. The method can involve the step of displacing a volume of fluid within the connector apparatus to the fluid column, wherein the ratio of the volume of displaced fluid to the volume of the fluid column ranges from approximately 1:2 to less than about 1:1 (e.g., about 3:4). Further, the method can comprise measuring changes to the pressure within the fluid column resulting from the contraction of tissue about the pressure compliant member.

The details of one or more examples are set forth in the accompanying drawings and the description below. Other features, objects, and advantages will be apparent from the description and drawings, and from the claims.

DETAILED DESCRIPTION

For purposes of illustrating the various aspects of the methods and systems claimed herein, the discussion below will be directed to describing exemplary embodiments used in urodynamic pressure sensing, as further described in the commonly-assigned application U.S. Ser. No. 15/456,062, filed on Mar. 10, 2017, titled "PRESSURE CATHETER AND CONNECTOR DEVICE," the entire contents of which are hereby incorporated by reference. It should be noted, however, that the elements and principles discussed herein are applicable to other applications. For example, the exemplary embodiments described herein are contemplated for use with any type of catheter wherein measurement of pressure within the body of a patient is desired. Further, discussion of methods and systems herein can be interchangeable with respect to specific aspects. In other words, specific discussion of one method or system (or components thereof) herein is equally applicable to other aspects as they relate to the system or method, and vice versa.

Figure 1:
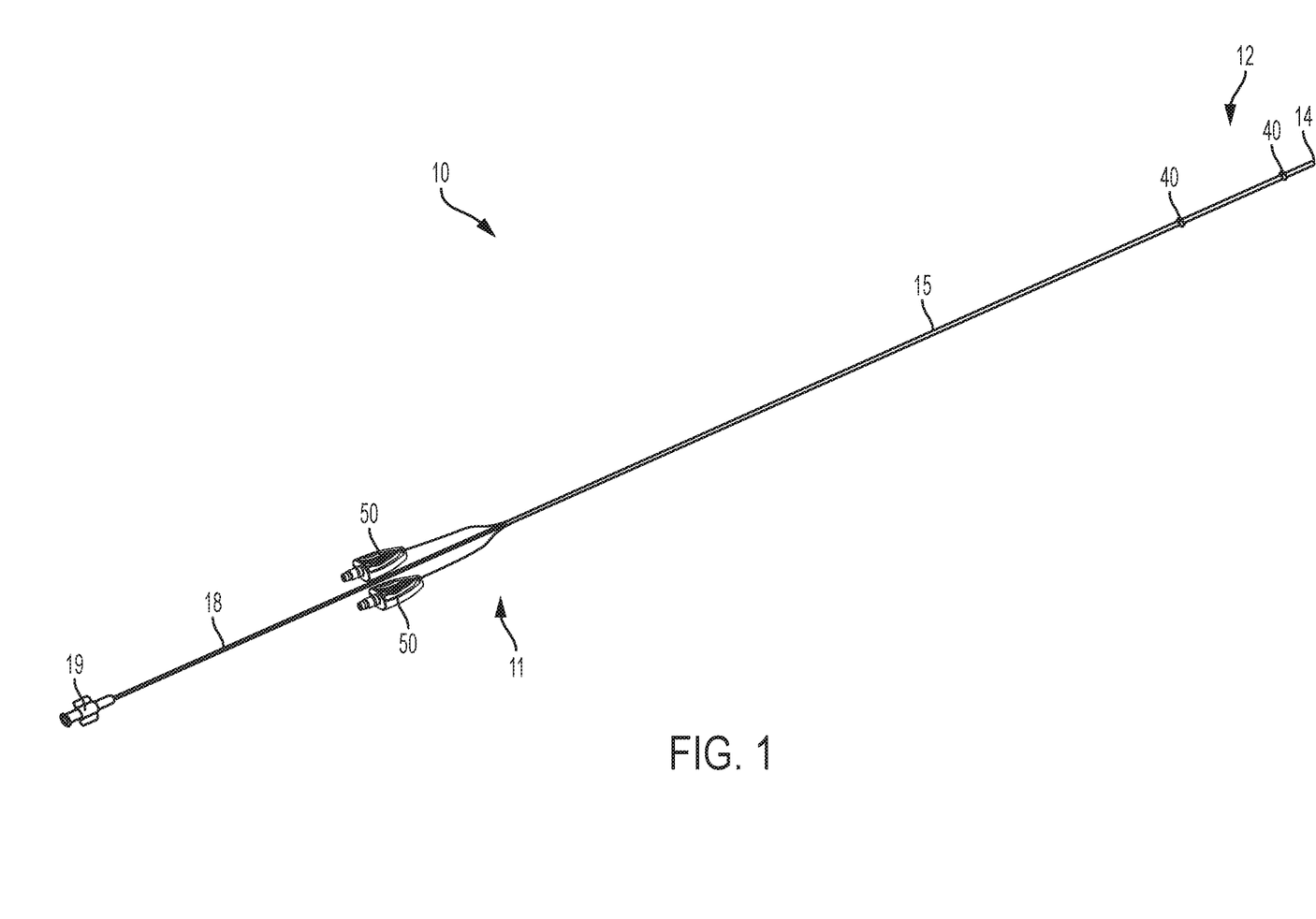
FIG. 1 is a perspective view of a catheter in accordance with a non-limiting exemplary embodiment.

FIG. 1 is a perspective view of a catheter in accordance with a non-limiting exemplary embodiment. As shown in FIG. 1, a pressure monitoring catheter 10 is disclosed comprising an elongate flexible fluid column catheter that is connectable to a pressure sensing apparatus by way of connector 50. An elongate center arm 18 extends from the proximal end 11 of the catheter 10 to a connector 19. The connector 19 in turn can be used to attach a syringe or other device used for the collection (e.g. aspiration) or delivery (e.g. infusion) of fluids to or from the cavity of the patient through holes 20 at the distal end 12 of the catheter 10. A data/power cable or wireless transmitter (not shown) connects the pressure sensing apparatus to a processor and monitor and/or database.

The catheter 10 can be detachably attached to a cable assembly which is structured to be coupled (either wired or wirelessly) to a processor and monitor. In one aspect where the cable assembly comprises a wired reusable assembly, the reusable interface cable assembly has, at its proximal end, an electrical connector configured to be connected to a processor and a monitor. In the aspect where the cable assembly is wirelessly coupled to a processor and/or monitor, the proximal end of the cable assembly comprises a wireless transmitter.

With reference to FIG. 1, the distal end 12 of the catheter 10 comprises a soft, pliant tip 14, which facilitates insertion of the catheter 10 into the patient. The soft tip 14 may preferably be formed of a material pliant enough to deflect or give as the tip 14 encounters a resistive force, such as the wall of the bladder. A low durometer plastic or elastomer, such as polyvinyl chloride (PVC) or polyurethane, is suitable, though other materials having a suitable rigidity/pliancy and are safe for use inside a patient can be used. The tip 14 can be formed from an elongated hollow tube 15 which extends from the tip 14 at its distal end 12 to one or more connector 50 on its proximal end 11.

With continued reference to FIG. 1, the hollow tube 15 can be formed of flexible, biocompatible material, such as PVC or a polyolefin, with sufficient properties, such as wall thickness, to resist collapse under normal conditions, and sized in length to extend from within a cavity (e.g., the alimentary canal or urinary tract) of a patient to outside the body of the patient. Thus, for example, the hollow tube 15 may range in length from 20 cm to 90 cm.

Figure 2:
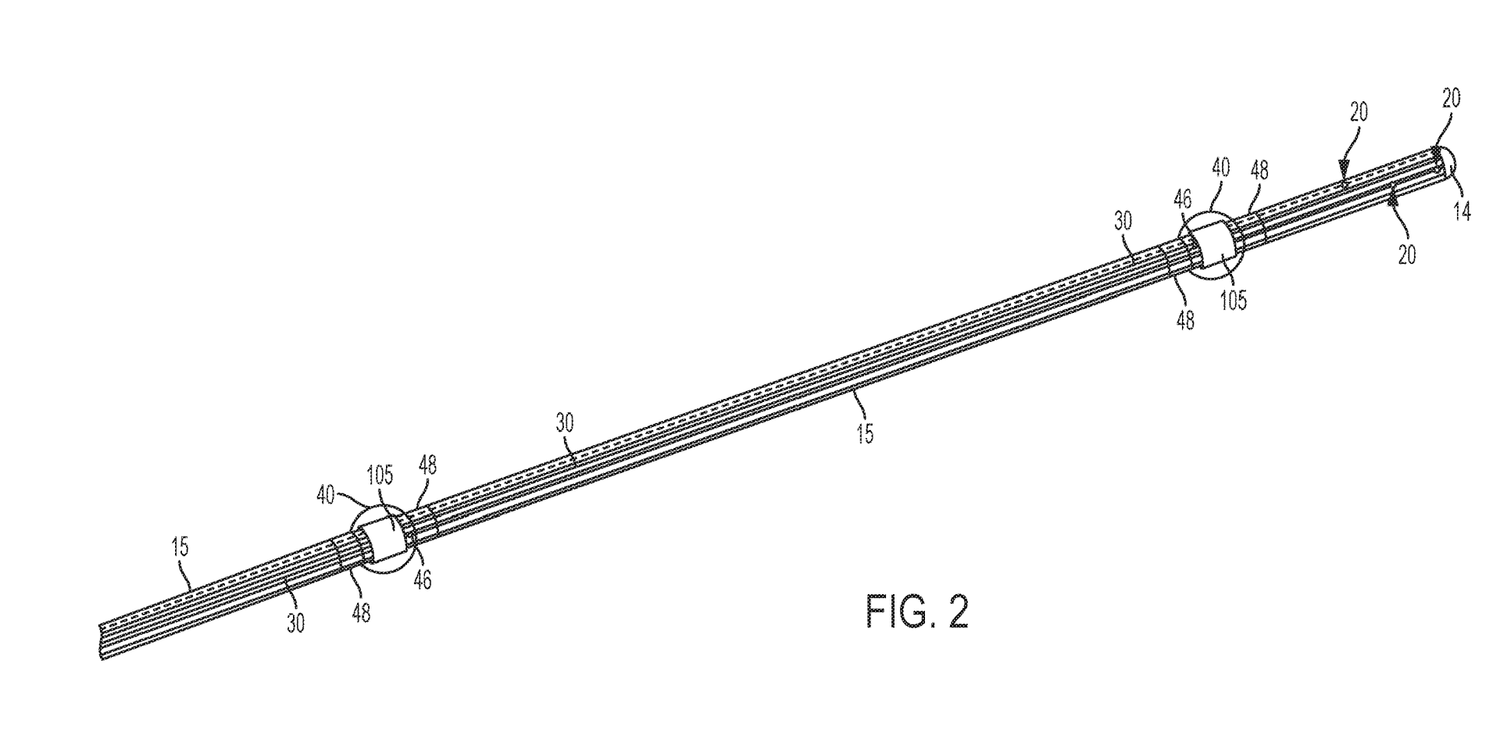
FIG. 2 is a close up perspective view of a portion of the catheter of FIG. 1.

FIG. 2 is a portion of the catheter of FIG. 1 to illustrate details thereof. As shown in FIG. 2, a plurality of holes or apertures 20 are formed through the wall of the hollow tube 15 immediately behind the tip 14. The number of holes 20 may vary, however. The holes 20 are distributed about the circumference of the outer hollow tube 15 and longitudinally about a distal end 12 of the catheter 10 to allow fluid to be aspirated or otherwise collected from the patient or infused or delivered into the patient during a procedure. A plurality of holes 20 is provided so that if any one or more holes 20 should become clogged or blocked, other holes 20 will be available for allowing passage of fluid. In an alternative aspect, slits, such as slit valves may be formed through the wall of the outer hollow tube 15 to provide for infusion and/or aspiration of fluids.

Figure 3:
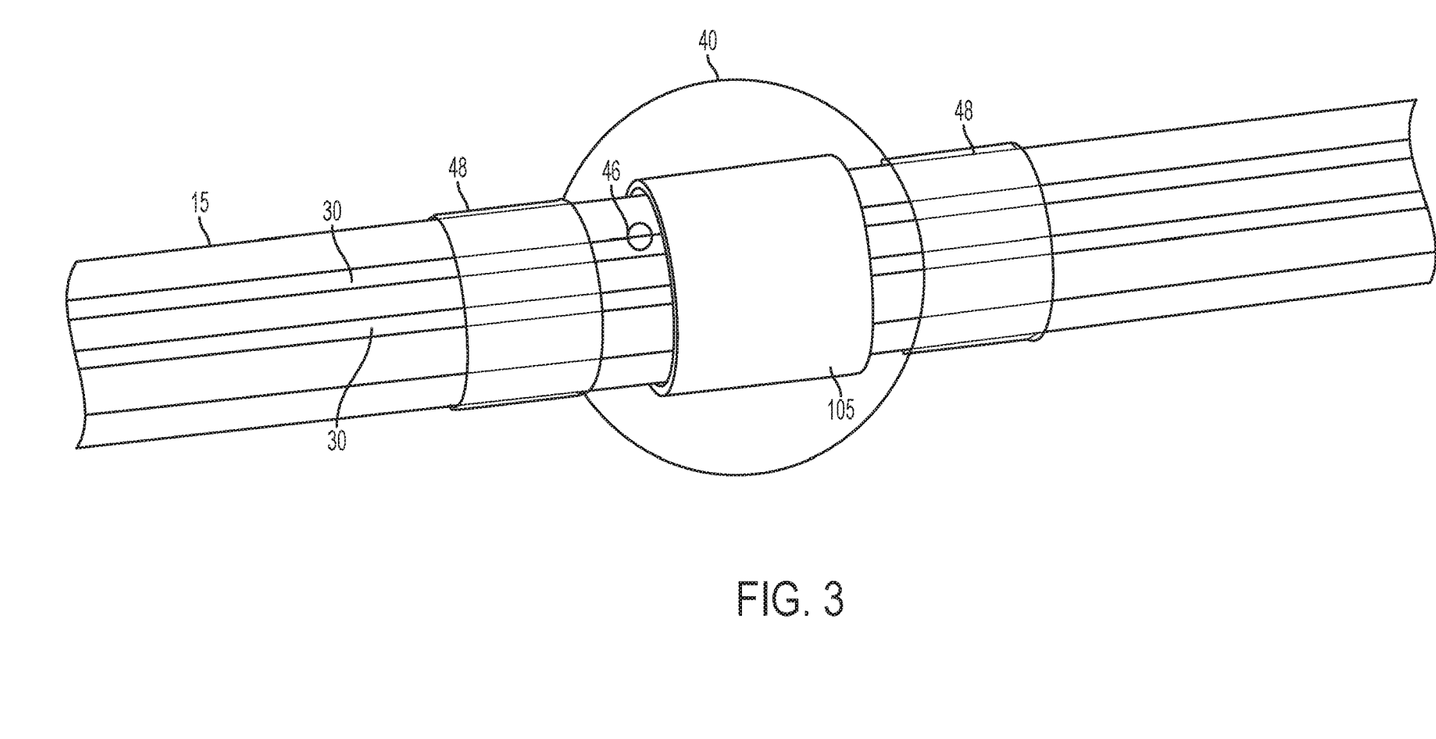
FIG. 3 is a further close up perspective view of a portion of the catheter of FIG. 1.
Figure 4:
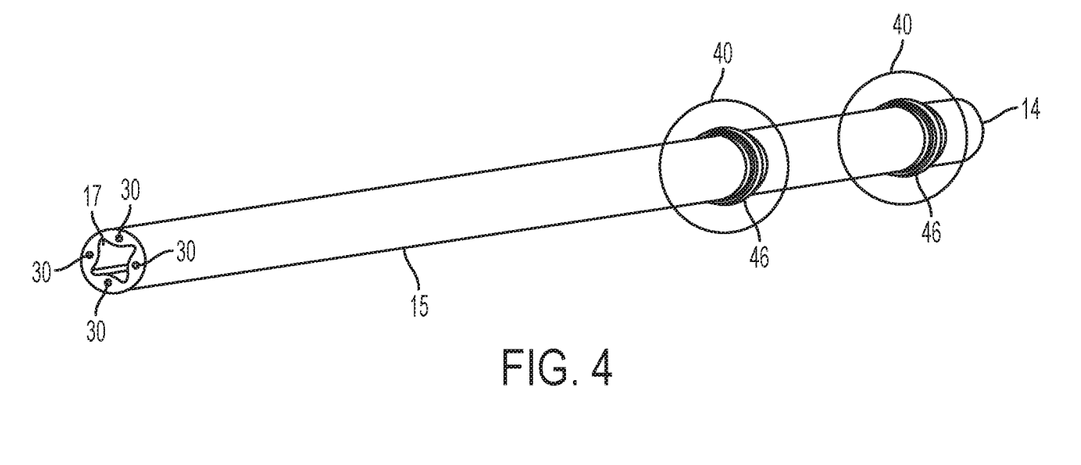
FIG. 4 is a cross sectional view of a portion of the catheter of FIG. 1.

With continued reference to FIG. 2 and referring now to FIGS. 3 and 4, the catheter comprises a central lumen 17 and one or more secondary lumens 30 that are disposed within the hollow tube 15. The central lumen 17 can be in fluid communication with holes 20. Additionally, the central lumen 17 can also be in fluid communication with a lumen of the elongate center arm 18 (best seen in FIG. 1). In some examples, the central lumen 17 has a hydraulic diameter ranging from about 0.75 to about 1.75 millimeters with a non-limiting exemplary diameter of 1.1 millimeters.

Figure 5:
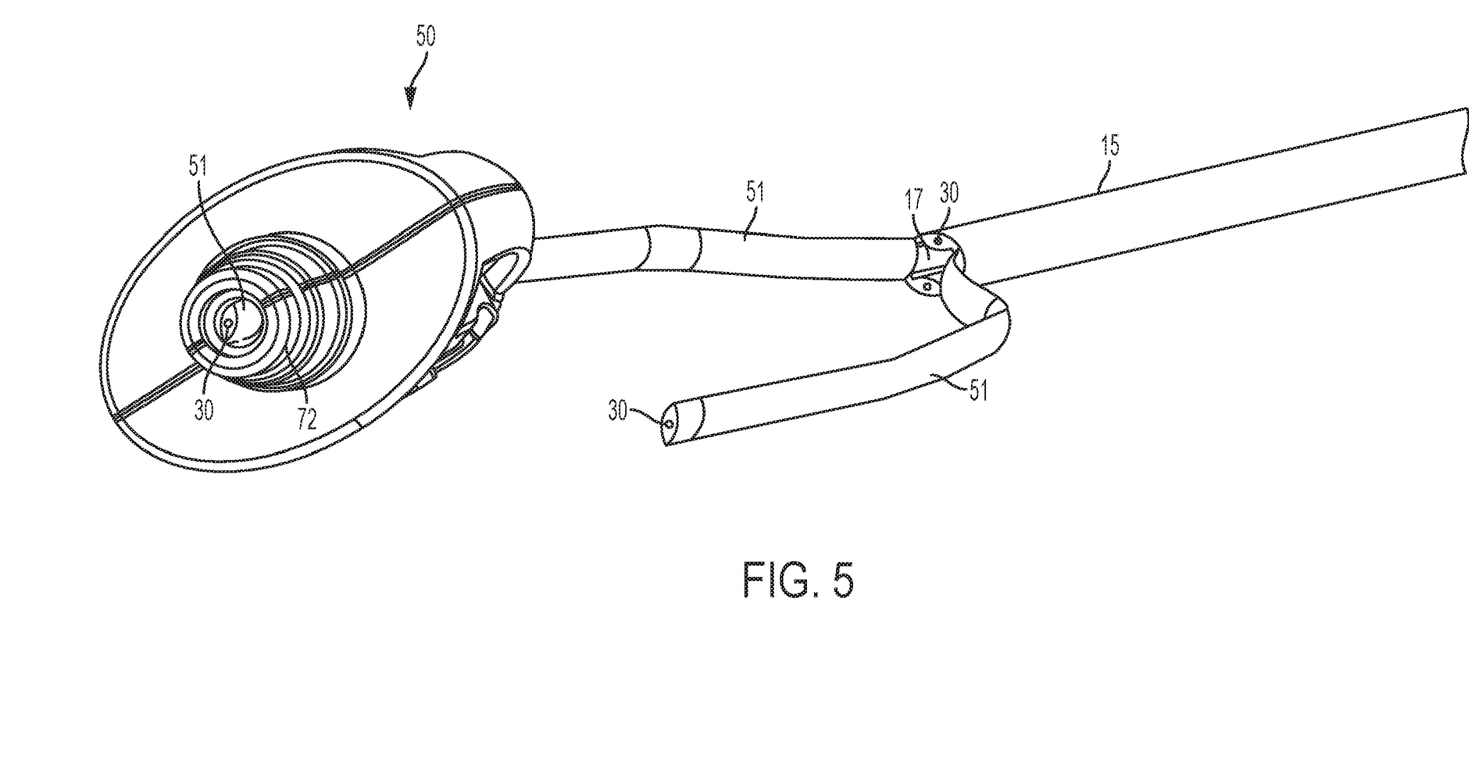
FIG. 5 is a semi-exploded perspective view of a distal end of the catheter of FIG. 1.

The secondary lumen 30 may be interchangeably referred to as "monitor lumen." Returning to FIGS. 3 and 4, each monitor lumen 30 comprises one or more flexible, biocompatible materials, such as polyurethane and is integrally formed from or with the sidewall of the hollow tube 15. The secondary lumen 30 is sized in diameter to fit within the hollow tube 15 and to leave adequate space for passage of fluids through central lumen 17. Referring now to FIG. 5, the secondary lumen 30 extends from the connector 50, (and sealed therewith), to the distal end 12 of the catheter 10. As seen from FIG. 5, the secondary lumen 30 extends from the hollow tube 15 of the catheter 10 body to the connector 50 by way of a flexible extension arm 51 which is integrally formed with the elongate hollow tube 15.

Referring back to FIGS. 3 and 4, a flaccid, pressure-compliant member (e.g., a balloon) 40 can be in fluid communication with the secondary lumen 30 and is positioned about the relatively non-compliant hollow tube 15. The pressure-compliant member 40, which is fluid-filled in one aspect, is structured to deflect or deform upon application of a force thereto, (e.g. an increase in pressure within the body cavity from the contraction of tissues within the body), and to expand again upon removal of the force therefrom (e.g. a subsequent decrease in pressure after a relaxation of the contracting tissues). Therefore, a particularly suitable pressure-compliant member 40 may be a medical grade balloon 40 formed of a thin-walled, flexible, low durometer material such as C-Flex® elastomer, which is relatively easily deformed with a small increase in pressure.

With reference to FIGS. 2 and 3, the balloon 40 may be formed as a substantially circular body disposed about and/or attached to an opening 46 of a secondary (or monitor) lumen 30 and/or heat-sealed at the ends 48 of the balloon 40. While a circular shape is illustrated, other shapes may be used. Fluid (e.g., air) may occupy the interior of the secondary lumen 30. In such cases, fluid may be at atmospheric pressure prior to use of the catheter 10. The secondary lumen 30 and the balloon 40 attached to the secondary lumen 30 (including any portion of the secondary lumen 30 that extends within the connector 50) may, therefore, form or define a fluid column which extends from inside the connector 50 to near the tip 14 of the catheter 10. When the catheter 10 is attached to complementary connector, as explained further below, the fluid column becomes filled, or "charged," with an additional quantity of fluid. The additional fluid charged into the fluid column partially fills the balloon 40 to a selected volume.

The material of the balloon 40 can be substantially pliant due to its thin wall and the low durometer material used in its construction, and the balloon 40 deforms easily and substantially with a given change in pressure external to the balloon 40. Further, the balloon material may not introduce any artifacts during pressure measurements. The material of the balloon 40 may, for example, have a Shore durometer hardness of about 30 A. Examples of materials for the secondary lumen 30 may be C-Flex® synthetic elastomer of 1-2 millimeters wall thickness, or any other similar material having similar durability and flexibility or other material having characteristics suitable for the designs and use specified herein. Regardless of the material employed, in some examples, less than 5 millimeters of mercury (Hg) of maximum external pressure may collapse the balloon 40 when its interior is vented to atmospheric pressure, though the balloon 40 can be designed to be operable at pressure ranges ranging from 0 millimeters Hg to 200 millimeters Hg. The collapse of balloon 40, before charging the fluid column as described, provides an accurate pressure signal.

With reference to FIG. 3, the balloon 40 may be attached to an end of the secondary or monitor lumen 30 in any appropriate manner. However, as illustrated in FIG. 3, the balloon 40 can be attached to the secondary lumen 30 by positioning the balloon 40 over opening 46 of the secondary lumen 30 and securing the balloon 40 about the circumference of the opposing ends 48 of the balloon 40. The balloon may be secured by laser welding, adhesive bonding, RF welding, induction welding, hot air welding, or other suitable methods for securing balloon 40 to the catheter 10.

As seen from FIGS. 3 and 4, the balloon 40 can be positioned about the exterior of the hollow tube 15 so that the interior volume of the balloon 40 is substantially laterally aligned with the apertures or opening 46 formed through the hollow tube 15 so as to be in fluid communication with the secondary (or monitor) lumen 30. Thus, the balloon is in fluid communication with the secondary lumen 30 and the charge-volume of fluid from the connector apparatus. While a single opening 46 is shown as providing fluid communication with the secondary lumen 30, in other aspects of the disclosure more than one opening may be present within a single balloon 40 corresponding to a single secondary lumen 30. In certain exemplary embodiments, more than one secondary lumen 30 (as shown more fully in FIG. 4) is used as more than one sensor balloon 40 is disposed about the catheter 10.

As may be appreciated, too high an internal fluid column pressure can reduce the sensitivity of the device for measuring pressure changes and may increase the susceptibility of the pressure monitoring to temperature-induced artifacts. Balloon 40 may burst due to its relatively fragile construction if over-pressurized. Accordingly, some such exemplary embodiments provide optimal balloon diameter and fluid column pressure. Further, some exemplary embodiments of the current disclosure balance total volume of the fluid column according to the volume of fluid within the secondary (or monitor) lumen 30, the total volume available within the balloon 40, and the balloon charge volume.

In accordance with one aspect of the disclosure, prior to placement on the catheter 10, the balloon 40 has a length ranging from about 8 millimeters to about 10 millimeters with one non-limiting exemplary length of about 9 millimeters. After the top and bottom portions of the balloon 40 are secured to the outside of the hollow tube 15 (e.g., through laser welding or other suitable method), the length of the inflatable portion of the balloon 40 can range from about 5 millimeters to about 8 millimeters with one non-limiting exemplary length of about 6 millimeters.

In some such aspects, the diameter of the balloon 40 can range from about 5 millimeters to about 8 millimeters with one non-limiting exemplary length of about 6 millimeters and the hollow tube 15 has an outer diameter ranging from about 1.5 millimeters to about 2.5 millimeters with one non-limiting exemplary diameter of about 2 millimeters. A balloon diameter that is too small may not provide enough space between the inner wall of the balloon 40 and the outer wall of outer tube 15 to create a sufficient amount of deflectable volume to accurately measure a patient-induced pressure event (e.g., coughing, flexing of alimentary canal tissues, etc.) before the balloon 40 "bottoms out" (e.g., touches) against the outer wall of the hollow tube 15.

In some examples, life, maximum pressure, and accuracy of the balloon may be a function of the separation distance between the inflated balloon 40 and the outer wall of hollow body 15 the catheter 10. As the pressure differential between the inside and outside of the balloon 40 increases, the balloon 40 may collapse and "wrinkle" toward the catheter 10. Under pressure, the collapsing balloon 40 may wrinkle and bear upon the hollow body 15, thus counteracting the external pressure with both internal pressure created from shrinking volume, and force applied against the hollow body 15. As more force is transmitted from the balloon 40 to the hollow body 15, the remaining internal force, as measured by the pressure transducer, becomes significantly lower than the actual external pressure.

In accordance with aspects of the present disclosure, a larger balloon diameter and a smaller catheter body create a larger "gap" between the wall of the balloon 40 and outside wall of the hollow tube 15. As the inflated balloon 40 is subjected to the oxygen-poor urine, or other body fluid, oxygen molecules immediately begin permeation and diffusion across the balloon membrane, reducing the volume of the charged balloon immediately. While nitrogen molecules diffuse slower, and are contemplated for use as an inflation fluid herein, they too can also migrate across the balloon membrane. A larger gap, in such cases, may not slow loss of gas, but may provide a more tolerable level of loss, thus increasing balloon life. Even without loss of gas, the balloon 40 has a maximum measurable pressure where wrinkles (i.e., collapsing surface of the balloon 40) touch the catheter 40. A measure of this maximum pressure correlates with the catheter life due to loss of gas over time.

Some examples of the present disclosure minimize dead space within the system which affects system accuracy and balloon life. In one aspect, a minimum of about 60% to 80% of the total closed system volume needs to be "working volume" while the other 20% to 40% of the total close system volume comprises "nonworking volume." The "working volume" comprises the volume of fluid within the balloon while the "non-working volume" comprises the volume of fluid within the monitor lumen and the interstitial spaces in the connector mechanism. The collapsing balloon 40 may wrinkle inward to accommodate both the collapsing balloon volume and the densifying of the fluid in the nonworking volume. In one aspect of the disclosure, the ratio of working volume to nonworking volume is greater than 2:1 in an effort to optimize maximum balloon pressure, high-end pressure accuracy, and balloon life. Advantageously, the balloon geometry described herein optimizes the inward "wrinkle" of the balloon 40 so that it may not collapse on itself which may negatively affect balloon performance.

While a smaller catheter diameter (e.g., 5-7 Fr) and a slightly larger diameter for the balloon 40 are certain aspects of the present disclosure, a smaller catheter may put constraints on the diameter of the infusion lumen. In addition, too large a balloon 40 may be over constrained (e.g., pre-pressurized simply by its relative size within the patient) when inflated within the a body cavity (e.g., the urethra), causing overstated "resting tones" sensed without the patient "squeezing", but in a relaxed state. Accordingly, the ratios presented herein may be considered illustrative, and balanced during practical use.

In one aspect of the disclosure, the internal volume of the balloon 40 ranges from about 90 microliters to about 120 microliters with one non-limiting exemplary volume of 100 microliters. In one aspect, the diameter of the secondary (or monitor) lumen 30 ranges from about 0.15 millimeters to about 0.35 millimeters with one non-limiting exemplary diameter of 0.25 millimeters. Based on an exemplary total length of the secondary lumen 30 of 20 centimeters to 90 centimeters, the total volume of fluid within the secondary lumen 30 can range from about 25 microliters to about 40 microliters with one non-limiting exemplary volume being 32 microliters. A charge volume (which may correspond to the amount of fluid introduced into the fluid column) can range from about 40 microliters to about 60 microliters with a non-limiting exemplary volume of about 50 microliters. The total volume of the fluid (e.g., air) column may be defined by the volume of the secondary (or monitor) lumen 30 and the interior chamber defined by the balloon 40 (e.g., the balloon volume). Accordingly, in one aspect of the disclosure, the volume of the fluid column can range from about 115 microliters to about 160 microliters with a non-limiting exemplary volume being about 132 microliters. As noted herein, the charge volume can refer to the total amount of fluid that is introduced into the fluid (e.g., air) column to "charge" or ready the catheter 10 for pressure measurement.

Figure 6:
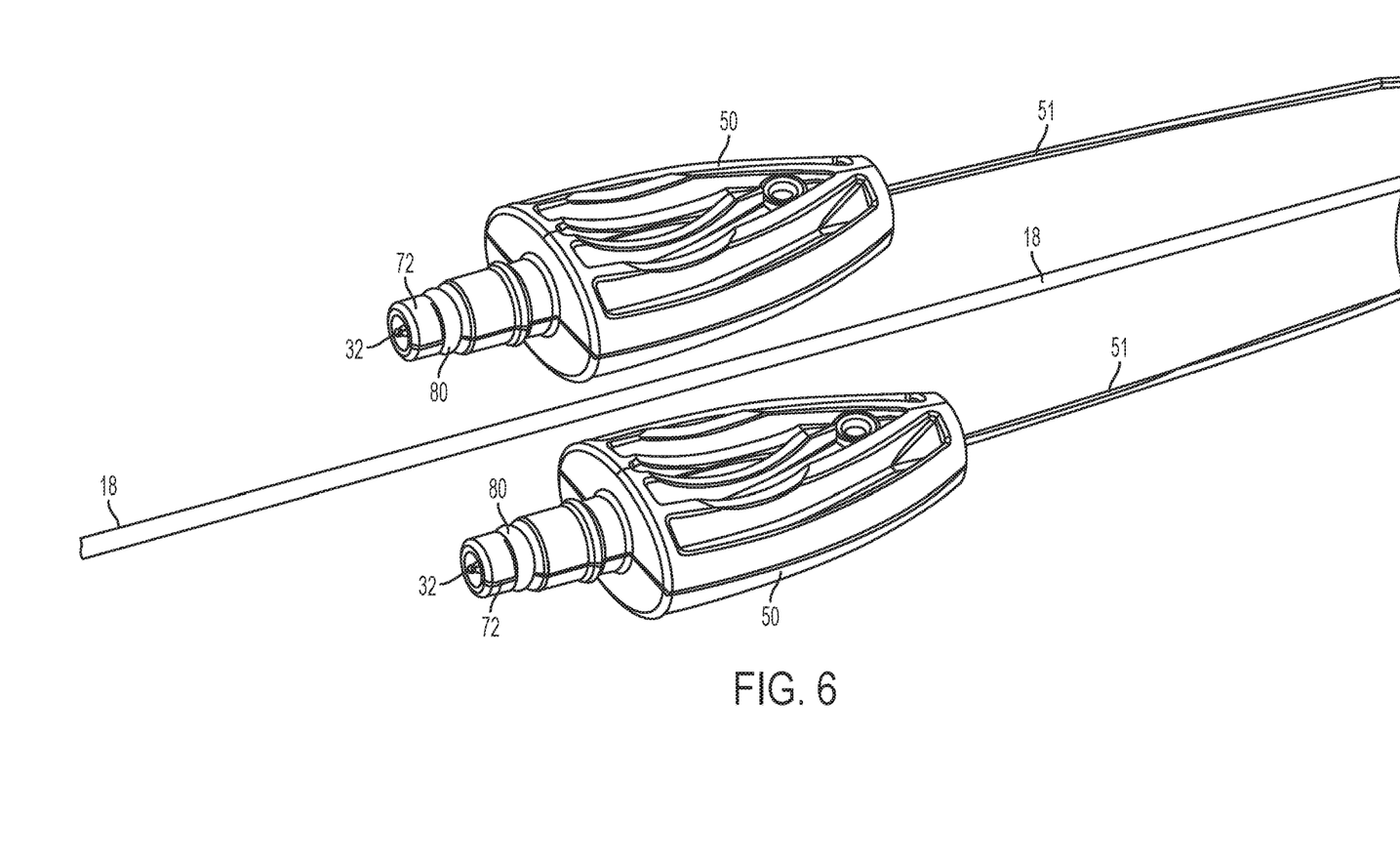
FIG. 6 is a close up perspective view of a portion of the catheter of FIG. 1 illustrating a first complementary connector according to a non-limiting exemplary embodiment.
Figure 7:
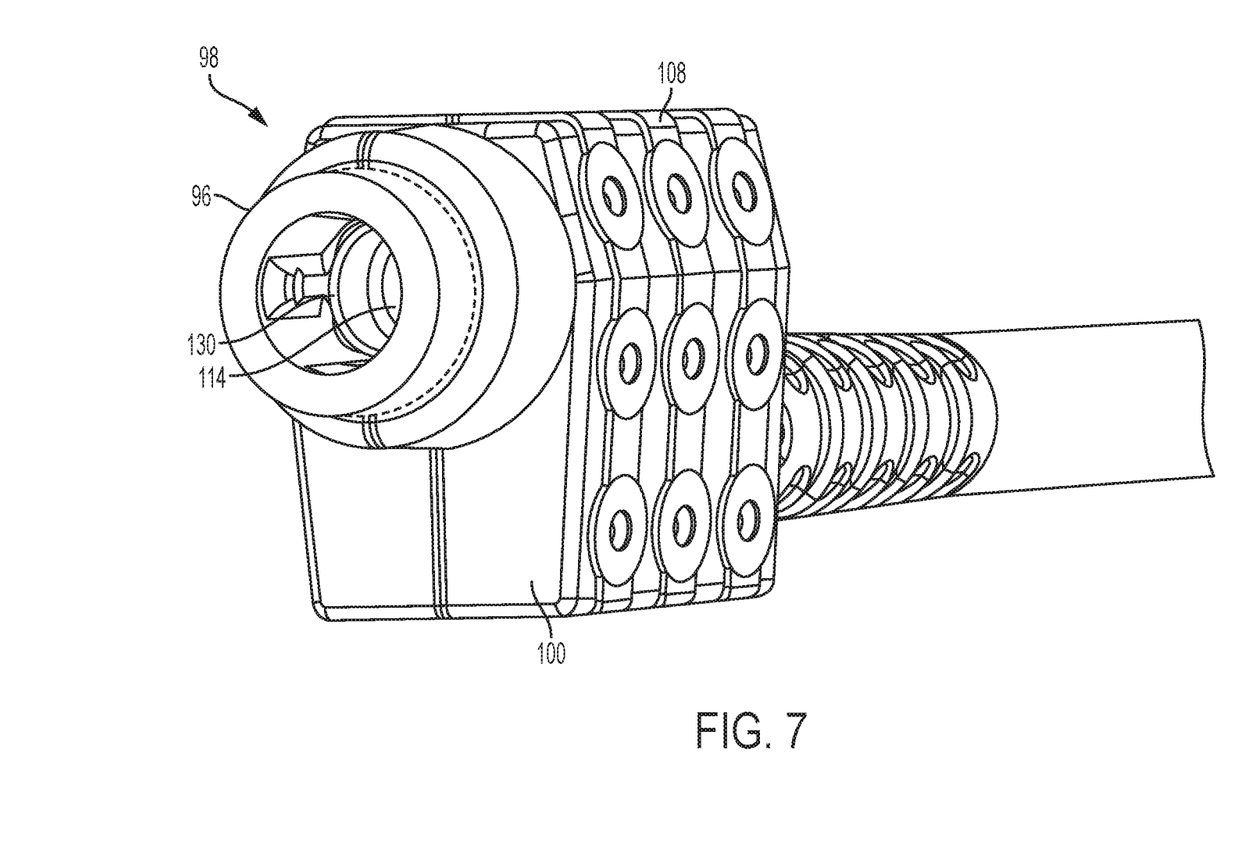
FIG. 7 is a perspective view of a second complementary connector in accordance with another non-limiting exemplary embodiment.
Figure 8A:
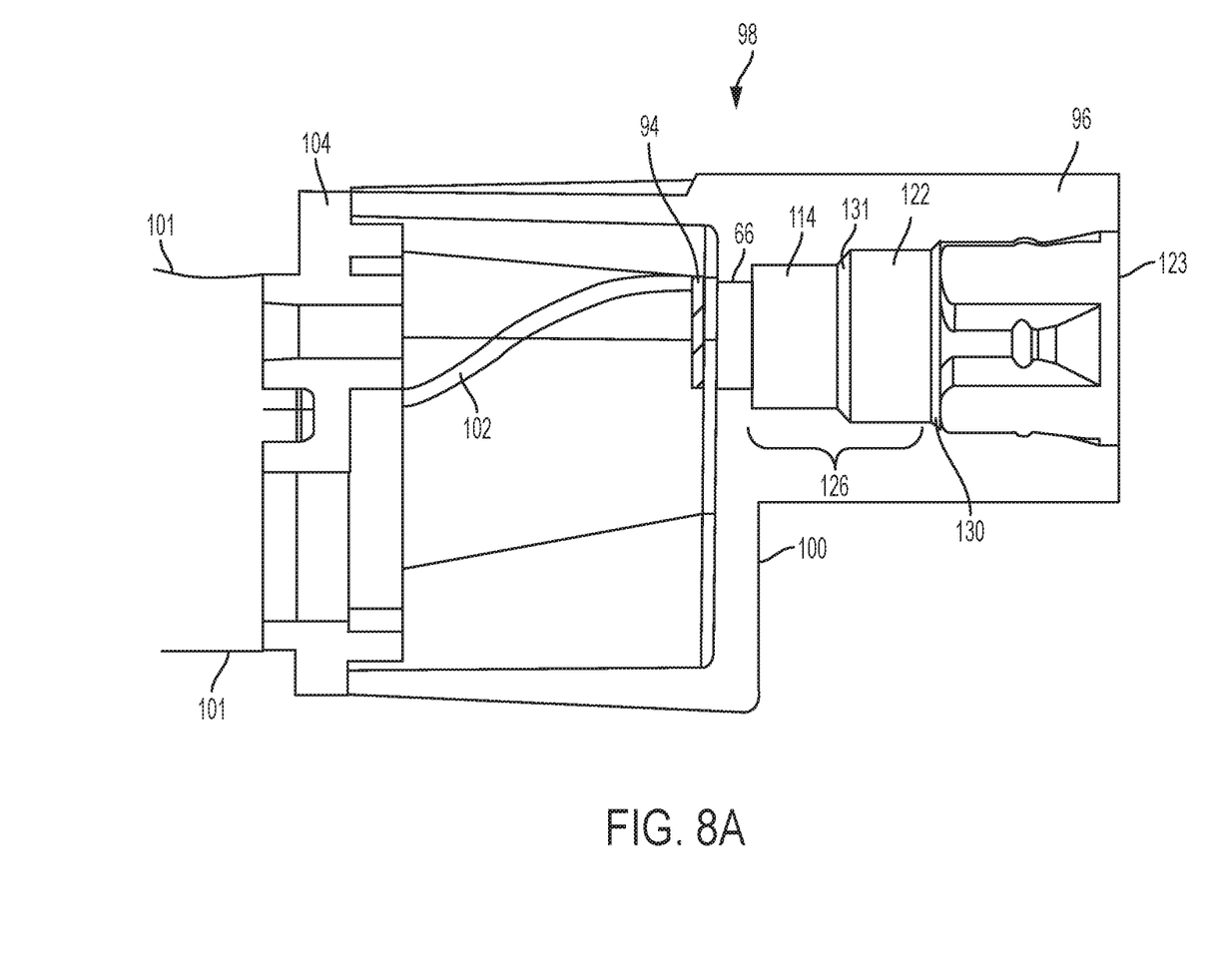
FIG. 8A is a cross sectional view of a portion of a second complementary connector in accordance with a non-limiting exemplary embodiment.
Figure 8B:
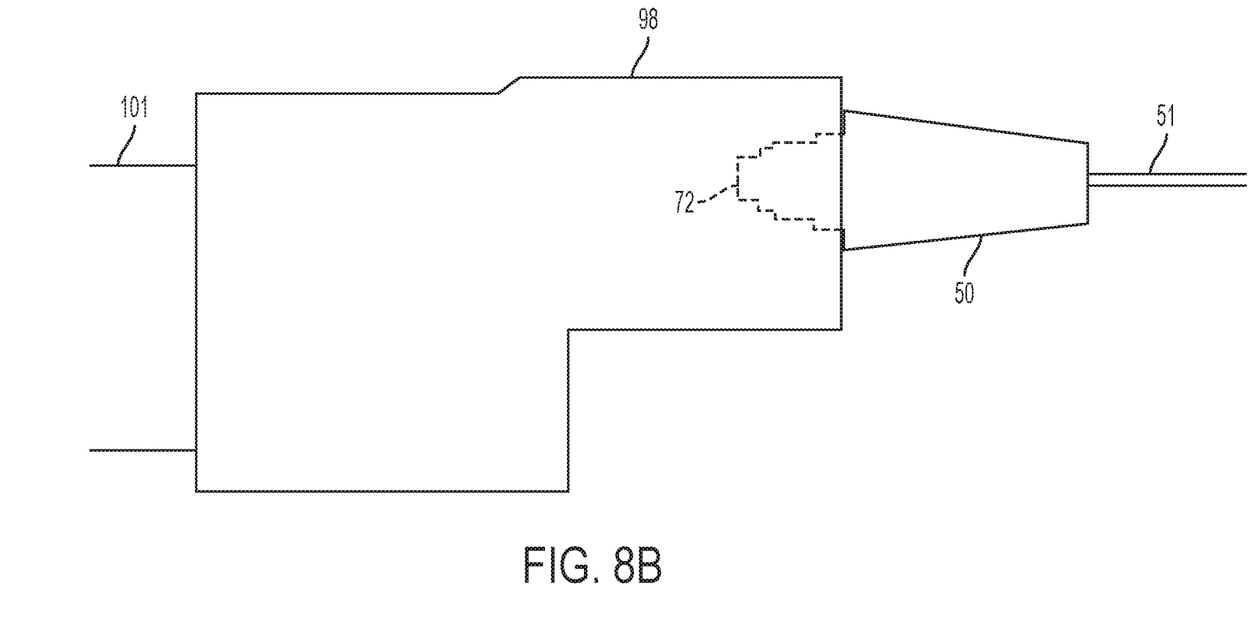
FIG. 8B is a front view of the first complementary connector of FIG. 6 connected to the second complementary connector of FIG. 7.

FIGS. 6-8 illustrate various portions of the catheter and a complementary connector. While FIG. 6 illustrates details of a first complementary connector 72, FIG. 7 illustrates details of a second complementary connector 98 that can receive the first complementary connector 72. FIG. 8A illustrates a sectional view of the second complementary connector 98 while FIG. 8B is a front view of a connected orientation of the first complementary connector and the second complementary connector. Referring to FIG. 6, the first complementary connector can be fixedly attached to the proximal end of the elongate member and comprises an internal lumen in fluid communication with the monitor lumen.

Referring to FIGS. 6 and 7, the second complementary connector can be removably connected to the first complementary connector. Referring to FIGS. 7 and 8A, the second complementary connector 98 has an internal bore or cavity 114 that is sized in internal diameter and length to frictionally receive the first complementary connector 72 (shown in FIG. 6) of the catheter 10. Upon insertion of the first complementary connector 72 in the bore 114 of the second complementary connector 98, the O-ring 80 becomes seated against an inner wall of the internal bore 114 to form a fluid-tight fit.

As seen in FIG. 8, the bore 114 and charging section 122 lying between the engagement section 123 of the second complementary connector 98 and the enclosure 100 of the proximal coupler 96 define an internal space 126 which contains a predetermined or selected volume of fluid (e.g., the charge volume) prior to insertion of the first complementary connector 72 into the bore 114 of second complementary connector 98. Thus, in an example, as the first complementary connector 72 is inserted so as to act like a pressurizing device (e.g., piston or plunger) into the bore 114 of second complementary connector 98, part of the volume of fluid contained within the internal space 126 of the bore 114 is displaced by first complementary connector 72 through the end 32 of monitor lumen 30 adding the volume of fluid to the fluid column. The displaced volume of fluid may be sufficient to "charge" or partially fill the balloon 40 with an appropriate amount of fluid to expand the balloon 40 to function with desired sensitivity responsive to a given range of pressure values. In other words, the effective fluid volume trapped in the fluid column is defined by the inward stroke or travel of first complementary connector 72, and its related components, from the point at which O-ring 80 passes flutes 130 until first complementary connector 72 is fully inserted in second complementary connector 98.

Referring again to FIG. 8A, at the distal end of the cable is a pressure detection device 94 which, when coupled to the catheter 10 by way of connector 50 (illustrated in FIG. 6), interfaces with the fluid column of the catheter 10 to detect changes in pressure (e.g., urodynamic pressure). With continued reference to FIG. 8A, a proximal extremity 66 of the enclosure 100 and the open proximal end 32 of the monitor lumen 30 are positioned in close proximity to the pressure detection device 94 housed within the enclosure 100, minimizing dead space in the system. The pressure detection device 94 may be, in a non-limiting example, a pressure transducer having a deformable diaphragm positioned toward the engagement section 123 of the second complementary connector 98. Wiring 102 extends from the pressure transducer through the enclosure 100 and to the proximal end of the cable 101 for communication to a processor.

With reference to FIG. 8A, the pressure detection device 94 is operable with a proximal coupler 96 structured within a second complementary connector 98, the proximal coupler 96 being sized to receive a first complementary connector 72 (illustrated in FIG. 7) from connector 50 of the catheter 10. The second complementary connector 98 has an enclosure 100 for housing the pressure detection device therein and an end cap 104 for capping the enclosure 100 and attaching the pressure detection device 94 to a tubular cable 101 of the reusable interface cable assembly. A protective cover 108 may also be provided on the reusable interface cable assembly sized to fit over the second complementary connector 98.

Upon insertion of the catheter 10 into the body cavity, the balloon 40 may be in a substantially deflated state. With charging, the balloon 40 becomes at least partially filled with fluid (e.g., air). Thus, depending on how much fluid is in the balloon 40 prior to charging, the balloon 40 may be anywhere from 40% to 70% filled to capacity with fluid following charging. In some examples, the balloon 40 may not be overfilled so as to reduce the chances of the structure of the balloon 40 being introduced into the signal. In other words, the flaccidity of the partially-filled working volume of balloon 40 can reduce the occurrence of aberrant effects in pressure detection due to temperature changes (for instance, from Charles's Law), or undesirable effects that may introduce signal artifacts due to the balloon wall internal forces, or external balloon compression from debris.

The low durometer material of the balloon 40 allows the surface of the balloon 40 to deform with an increase in pressure. Therefore, a minimum of 1 millimeter Hg increase in body cavity pressure may cause deformation of the balloon 40 and, in turn, modify the pressure in the fluid column within the balloon 40 and secondary lumen 30. The change in pressure is translated down the fluid column to the diaphragm of the pressure detection device (best seen in FIG. 8). Deflection of the diaphragm resulting from an increase in pressure can be converted to an electrical signal by the transducer and is relayed to the monitor through the cable 101 or wirelessly. Similarly, a subsequent decrease in body cavity pressure can also be relayed by subsequent expansion of the balloon 40. While a pressure transducer has been specifically described, other means of detecting pressure changes known in the art are contemplated for use herein.

Advantageously, aspects of the present disclosure provide for wider pressure ranges. The larger diameter balloon 40 and outer tube 15 combination allows the catheter 10 to measure a larger pressure range before "bottoming" out against the outside wall of the outer tube 15. Moreover, the balanced ratio of charge volume, secondary or monitor lumen volume, and balloon volume/geometry may optimize the sensitivity of the system to better measure cavity pressure. In addition, the balancing of these elements may minimize damping of the pressure signal which increases the speed and resolution of the pressure measurements within the patient.

In accordance with an aspect of the disclosure, the ratio of the volume of fluid displaced (e.g., charge volume) to the volume of the fluid (e.g., air) column ranges from about 1:2 to about 1:1 with a non-limiting exemplary range of 1:2 to 3:4. In other words, in an aspect of the disclosure, the charge volume of the catheter 10 is approximately ½ to ¾ of the volume of the fluid column. Advantageously, such embodiments maximize space (and/or volume of fluid) available for charging while also increasing the range of pressure measurements.

In another aspect, the ratio of the longitudinal length of the balloon 40 to diameter of the balloon 40 ranges from about 0.75:1 to about 1.5:1. In another aspect of the disclosure, however, the ratio of the longitudinal length of the balloon 40 to the diameter of the balloon 40 ranges from about 1:1.5 to about 1:2. The ratio of the diameter of the balloon 40 to the diameter of the outer tube 15 may also be a factor in precision operation of aspects of the disclosure. In still another aspect of the disclosure, the ratio of the diameter of the outer tube 15 and the diameter of the balloon 40 ranges from 1:2 to 1:5.

Figure 9:
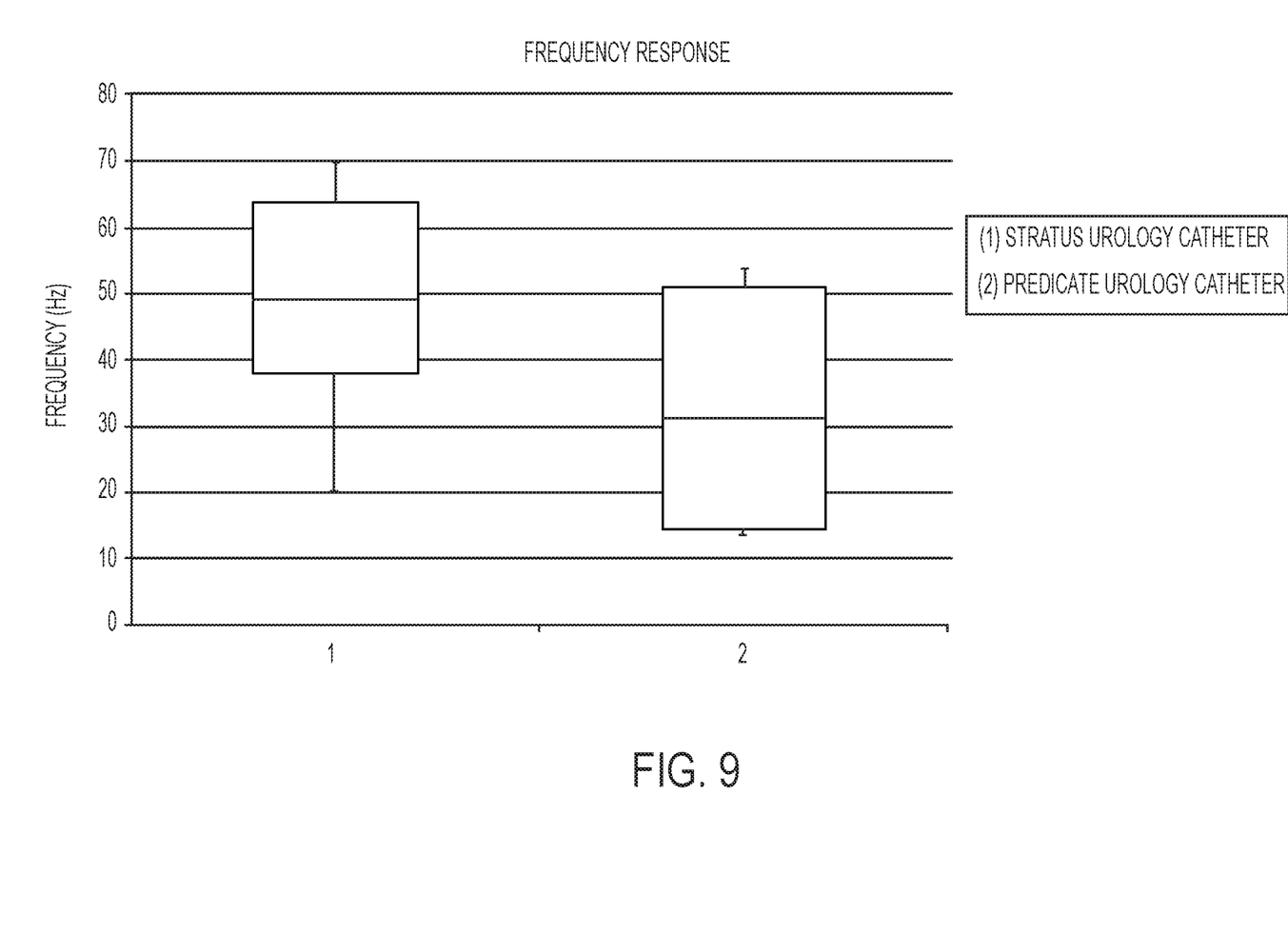
FIG. 9 is a whisker-plot showing improved frequency of detection of devices in accordance with a non-limiting exemplary embodiment.
Figure 10:
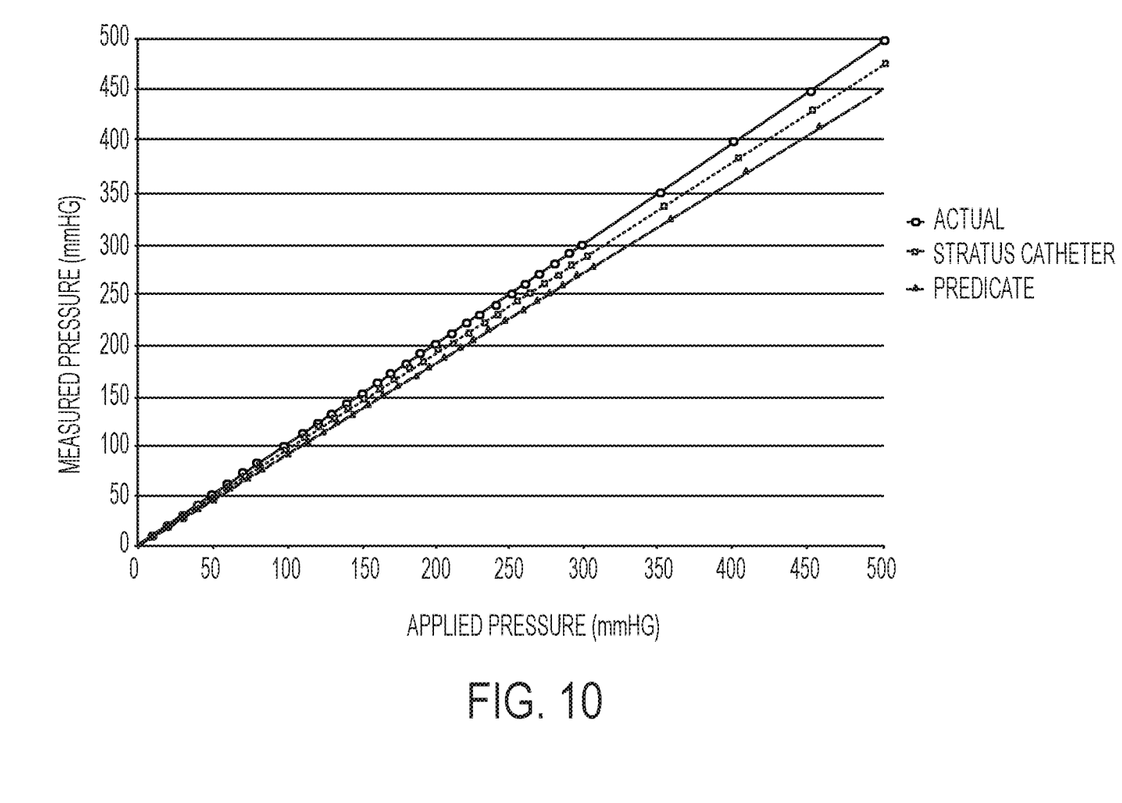
FIG. 10 is a graph showing improved pressure detection of devices in accordance with a non-limiting exemplary embodiment.

FIGS. 9 and 10 show examples of improvements of the present disclosure over prior art catheters. FIG. 9 illustrates the test results of the operational frequency of signals detected by the pressure detection device located in the second complementary connector 98 over a course of tests. The test results demonstrate a significantly higher operational frequency of measurements. The higher operational frequency yields significantly more precise measurements of pressure as well as higher granularity or finer measurements of pressure changes. For example, a coughing event that creates contraction of tissues within the body is a "high-frequency" event that cannot be adequately detected with prior art devices.

FIG. 10 illustrates a plot of actual pressures applied to a pressure-compliant member plotted against a comparison of measured pressure and applied pressure. The test results demonstrate the improved ability of aspects of the disclosure to measure actual pressure applied to the pressure-compliant members particularly as the amount of pressure applied increases. Advantageously, the disclosure allows for greater amounts of beginning pressures within the balloon 40 which results in a longer lasting testing time.

In accordance with an aspect of the disclosure, and as best seen in FIG. 2, a catheter marker band 105 can be provided on the catheter shaft. The marker band 105 can be a short, thin-wall tube or wire made from gold, tungsten, platinum or other dense metal and is placed on the a catheter shaft to provide high levels of visibility under fluoroscopy (radio-opacity). This can allow medical practitioners to precisely locate the catheter features deep within the body. In some examples, the marker band 105 can be made from compounding tungsten powder into a biocompatible polymer. Non-limiting examples of useable polymers include high-density polyethylene, polyamides, fluoropolymers (e.g., polytetrafluoroethylene), polyolefin, and PVC. While specific reference to tungsten is made herein, it is understood that other radiopaque materials are contemplated for use, including, but without limitation, platinum iridium, gold, tantalum, platinum, tungsten carbide, and the like. Such examples advantageously eliminate multi-step forming processes used in conventional devices to create seamless small diameter tubes or wire bundles and/or specialized manufacturing equipment to secure metal bands to the polymer catheter tip so that they do not fall off during use (e.g., a medical procedure). Accordingly, such examples of the present disclosure are less costly and time consuming relative to conventional devices whereby a metal band is provided on the catheter shaft.

In accordance with an aspect of the disclosure, tungsten is cryogenically ground to a powder having a particle size ranging from 5 to 20 µm. The tungsten powder is then placed in a batch mixer with polymer beads where it is heated and mixed together to form a polymer-tungsten composition. The resulting composition is formed into an elongate hollow tube from which the bands 105 are cut or otherwise created. Tungsten creates a dense band that is radiopaque in a fluid of radiopaque contrast media such as iodine or barium. In accordance with an aspect of the disclosure, bands 105 are customized using the same polymer specified for the catheter 10 shaft to allow heat bonding of the band 105 to the outer wall of hollow tube 15 for a more secure assembly.

In some examples, tungsten loadings within the thermoplastic polymer range from 50% to 80% by weight to meet radio-opacity requirements. The compounded, heated material is extruded into tubes that can be easily applied to the catheter 10. For instance, the tungsten-polymer tube can be placed over the exterior of the catheter 10 so that it is frictionally fit (or otherwise secured) about the exterior of the outer tube 15.

In some such examples, the interior diameter of the tungsten-polymer tube can be configured to approximate the outer diameter of the outer tube 15 of catheter 10. Further, in certain aspects, the tungsten-polymer tube can be placed over the outer diameter of the outer tube 15 but within the balloon 40 (e.g., centrally within the balloon 40). In some such aspects, the opening being surrounded by the hollow pressure compliant member, the radio opaque band 105 is circumscribed on the hollow tube 15 such that the radio opaque band does not cover the opening 46 on the monitor lumen 30. In this manner, the precise location of each "sensor" (i.e., balloon 40) is known to the practitioner. In this instance, the longitudinal length of the tungsten-polymer tube can be sized to be less than the longitudinal length of the balloon 40 as it is disposed on the catheter 10. For example, in the instance where the longitudinal length of the functioning balloon is 6 millimeters, the longitudinal length of the marker band 105 formed from the tungsten-polymer tube is less than 6 millimeters and, in one non-limiting example, has a longitudinal length of 4 millimeters.

In another aspect of the disclosure, a plurality of marker bands 105 are laser welded or otherwise secured to the outside wall of the catheter 10 on opposing sides of balloon 40 and, for example, placed over the portion of the balloon 40 that is welded to the outside wall of catheter 10. In this manner, the location of the balloon 40 within the patient is located between the two radio-opaque markers 105. In this aspect, the marker bands 105 have a longitudinal length that ranges from 4 millimeters to 6 millimeters. In yet another aspect of the disclosure, a radiopaque cap or blunt end is formed from the composition referenced above and disposed about a distal end of the catheter 10. The distal end of the catheter 10 is spaced a known distance from a balloon 40 on catheter 10 and therefore provides a marker within the body of the patient.

Various examples have been described. These and other examples are within the scope of the following claims.

The invention claimed is:
1. A pressure-sensing catheter for detecting pressure changes within a cavity of a patient, comprising:

an elongate member comprising a proximal end, a distal end and a central lumen extending from the proximal end to the distal end;

a first monitor lumen positioned within the elongate member between the central lumen and a wall of the elongate member, the first monitor lumen extending from the proximal end to the distal end, the first monitor lumen having a volume of 25 microliters to 40 microliters;

a first pressure-compliant member defining an interior chamber, the first pressure-compliant member being hollow and in fluid communication with the first monitor lumen, the first pressure-compliant member being disposed about an exterior of the elongate member, the first pressure-compliant member comprising a balloon, wherein a ratio of a diameter of the elongate member and a diameter of the balloon ranges from 1:2 to 1:5, and wherein the first monitor lumen and the interior chamber of the first pressure-compliant member define a fluid column;

a connector apparatus disposed about the proximal end and in fluid communication with the first monitor lumen, the connector apparatus comprising a first complementary connector and a second complementary connector, the first complementary connector and the second complementary connector being connectable to each other in a complementary fashion, at least one of the first complementary connector and the second complementary connector being fluidly coupled to the fluid column, one of the first complementary connector and the second complementary connector comprising a pressurizing device having an O-ring and the other of the first complementary connector and the second complementary connector comprising a bore and a flute that is defined at an inner wall of the other of the first complementary connector and the second complementary connector, wherein, when the pressurizing device is inserted into the bore and after the O-ring passes the flute, the pressurizing device is configured to displace a volume of fluid located within the bore into the fluid column, wherein a ratio of the volume of displaced fluid to the volume of the fluid column is at least about 1:2 and less than about 1:1 wherein the volume of fluid located within the bore and displaced into the fluid column is defined at the bore and a charging section, and wherein the O-ring of the pressurizing device encounters the bore and charging section after passing the flute.

2. The pressure-sensing catheter of claim 1, wherein the ratio of the volume of displaced fluid to the volume of the fluid column ranges from about 1:2 to about 3:4.

3. The pressure-sensing catheter of claim 1, wherein the ratio of the volume of displaced fluid to the volume of the fluid column is 1:2.

4. The pressure-sensing catheter of claim 1, wherein the fluid is air.

5. The pressure-sensing catheter of claim 1, wherein a ratio of the diameter of the balloon to a longitudinal length of the balloon is in the range of about 0.75:1 to about 1.5:1.

6. The pressure-sensing catheter of claim 1, wherein the first complementary connector is fixedly attached to the proximal end and comprises an internal lumen in fluid communication with the first monitor lumen.

7. The pressure-sensing catheter of claim 6, wherein the second complementary connector is removably attached to the first complementary connector and wherein the second complementary connector comprises a pressure detection device that is configured to transmit a signal to a processor, the signal corresponding to a change in pressure in the first pressure-compliant member.

8. The pressure-sensing catheter of claim 1, further comprising a second monitor lumen positioned within the elongate member between the central lumen and the wall of the elongate member, the second monitor lumen extending from the proximal end to the distal end, and being circumferentially spaced apart from the first monitor lumen.

9. The pressure-sensing catheter of claim 8, further comprising a second pressure-compliant member in fluid communication with the second monitor lumen, the second pressure-compliant member disposed about an exterior of the pressure-sensing catheter and distal from the first pressure-compliant member.

10. The pressure-sensing catheter of claim 1, wherein the first monitor lumen has a length of 20 cm to 90 cm.

11. The pressure-sensing catheter of claim 1, wherein the monitor lumen is formed from the wall of the elongate member.

12. The pressure-sensing catheter of claim 11, wherein the central lumen is configured for a passage of fluid therethrough.

13. The pressure-sensing catheter of claim 12, wherein the central lumen has a hydraulic diameter ranging from about 0.75 mm to 1.75 mm.

* * * * *